United States Patent [19]
Furnish et al.

[11] Patent Number: 5,470,328
[45] Date of Patent: Nov. 28, 1995

[54] SURGICAL INSTRUMENT HANDLE AND ACTUATOR MEANS

[75] Inventors: Greg Furnish, Lawrenceville; Michael Hipps, Roswell, both of Ga.

[73] Assignee: Snowden-Pencer, Inc., Tucker, Ga.

[21] Appl. No.: 278,632

[22] Filed: Jul. 21, 1994

[51] Int. Cl.⁶ .................................................. A61B 17/32
[52] U.S. Cl. .............................. 606/1; 606/205; 606/208
[58] Field of Search ................................. 606/205–209, 606/1, 171, 142, 143, 139, 108; 128/751–753

[56] References Cited

U.S. PATENT DOCUMENTS

| | | | |
|---|---|---|---|
| 2,898,916 | 8/1959 | Kammer | 606/139 |
| 4,248,233 | 2/1981 | Zeppelin et al. | 606/207 X |
| 4,590,936 | 5/1986 | Straub et al. | |
| 4,598,711 | 7/1986 | Deniega | 606/143 |
| 4,644,651 | 2/1987 | Jacobsen | |
| 4,777,948 | 10/1988 | Wright | 606/171 |
| 4,950,273 | 8/1990 | Briggs | |
| 4,957,500 | 9/1990 | Liang et al. | 606/205 X |
| 5,009,661 | 4/1991 | Michelson | 606/205 X |
| 5,195,505 | 3/1993 | Josefsen | |
| 5,199,419 | 4/1993 | Remiszewski et al. | |
| 5,250,073 | 10/1993 | Cottone, Jr. | 606/206 |
| 5,273,519 | 12/1993 | Koros et al. | 606/171 X |
| 5,304,203 | 4/1994 | El-Mallawany et al. | 606/205 X |
| 5,333,238 | 8/1994 | Holmes | 606/205 X |
| 5,342,391 | 8/1994 | Foshee et al. | 606/205 |

FOREIGN PATENT DOCUMENTS

WO81/03122   12/1981   WIPO.

Primary Examiner—Stephen C. Pellegrino
Assistant Examiner—Michael Peffley
Attorney, Agent, or Firm—Needle & Rosenberg

[57] ABSTRACT

The present invention provides a hand-held surgical instrument with an improved handle, the instrument being of the type generally comprised of a handle and a tool with a body member having at least one articulated member thereon. The handle of the present invention has an elongated base, an elongated lever with an actuator arm projecting into the base and a means for connecting the lever and base at a predetermined point on the base, which mimics a natural pivot point of the surgeon's hand. A means for actuating the surgical tool by moving an actuator rod distally by closing the handle lever, means for biasing the lever in an open position, and support feet providing a stand for the instrument are also provided.

18 Claims, 3 Drawing Sheets

SURGICAL INSTRUMENT HANDLE AND ACTUATOR MEANS

BACKGROUND OF THE INVENTION

1. Field of the Invention

This invention relates to handles for surgical instruments. In particular, this invention relates to an improved handle for hand held surgical instruments of the type having a tool with at least one articulated member thereon wherein the handle has a means for actuating the articulated member.

2. Background Art

Surgery is a learned art requiring many hours of advanced training and skills development that extends far beyond a thorough understanding of the medical principals involved, e.g., anatomy, physiology, principals of wound healing, and the like. The surgeon must also develop hand to eye coordination and acquire skills in the art of atraumatic tissue manipulation utilizing a variety of highly specialized surgical instruments.

The surgical instrument actually becomes an "extension" of the surgeon's hand. The surgeon must develop an ability to "feel" and respond, often delicately yet firmly, through his surgical instruments. Accordingly, there exists a need for instrument handles which are sensitive, responsive and ergonomically designed to augment the natural motions of the human hand.

The apposition between thumb and the index finger is the most sensitive and most often used means for delicate touching or for picking up small objects in every day affairs. Prior to the present invention, however, there were no surgical instrument handles designed to fully utilize the sensitive and delicate opposition capabilities of the thumb and index finger for movement of the lever arm of an instrument handle.

The actuating mechanism for handles of currently available surgical instruments are usually configured such that the pivot point is located between the handle lever and the articulated member (a forwardly located pivot point). The handle can have either one or two lever arms which are moveable about the pivot point. Such configuration is opposite to the natural pivot points of the hand.

One example of prior art handles of the type described above is the conventional "scissors-type" handle with a forward pivot point, e.g., Mayo or Metzenbaum scissors, or Debakey forceps. The scissors-type handle design usually lacks a means for biasing the instrument tool in an open position. Of necessity, therefore, these scissors-type handles have finger and thumb rings located at the free ends of the lever arms which provide a means for receiving force and balancing the instrument when both opening and closing the lever arms of the handle.

The scissors-type handles are usually held by inserting the thumb through the thumb ring, balancing the scissors against the index finger and inserting one or more of the remaining digits into the finger ring of the opposite lever. Movement of the lever arms is accomplished by apposing the thumb and digits which are in the finger ring. This design requires increased muscular effort to open and close the levers and therefore fatigues the hand of the surgeon.

A second example of the forward pivot point configuration is the "pliers-type" handle which is functionally similar to the scissors-type handle but without finger rings. In this configuration, movement of the levers from the open to the closed position is accomplished by closing the palm of the hand in a squeezing motion. A bow spring or other spring configuration located between the lever arms is sometimes included as a means to bias the handle in an open position to compensate for the lack of finger rings.

Neither the scissors-type nor the pliers-type handles are capable of being held and moved by the tips of the fingers, which results in a significant loss in sensitivity.

A third type of handle utilizes an actuator having two bowed springs connecting a rearwardly projecting actuator rod to handle levers which pivot about a forward pivot point. Although this handle may be held in a manner which allows for fingertip control, the forwardly located pivot point, opposite from the natural pivot point of the hand, results in loss of leverage and decreased sensitivity of the instrument. For fingertip control, the surgeon must sacrifice leverage by placing the fingertips away from the lever ends and closer to the forward pivot point.

One type of instrument which utilizes a rearwardly located pivot point is the forcep e.g., Adison, Potts-Smith, or general tissue forcep. Forceps utilize the thumb and index finger in a "pencil" grip fashion. However, forceps are not designed to activate an articulated member of a tool e.g., a needle holder, retractor, or hemostat. Rather the distal ends of the forcep lever arms actually comprise the tool itself.

Accordingly, there is a need in the art for a more sensitive and ergonomic instrument handle which is designed to functionally mimic and create functional harmony with the natural gripping mechanism and motion which exists between the thumb and index finger of the human hand. There is also a need in the art for a surgical instrument handle which is simpler to manufacture, assemble and disassemble than the prior art.

SUMMARY OF THE INVENTION

The present invention provides a surgical instrument with an improved instrument handle having a base and lever including an actuating arm which projects into the body of the base and is connected to the base at a predetermined pivot point. The instrument is designed to be held in a "pencil grip" or "Vardon golf grip" position; both of which are natural gripping relationships between the index finger and opposable thumb.

The handle of the invention functionally resembles the natural pivot points of the metacarpo-phalangeal joint of the index finger when the handle is held in the pencil grip fashion or of the carpo-metacarpal joint of the thumb when held in the golf grip manner. The handle of the present invention operates with fingertip control from the ends of the lever which increases leverage and sensitivity. The ergonomic design permits the surgeon to transfer force in a direct linear relationship from the hand to the articulated member of the surgical tool with precision, ease and delicacy.

The present invention also provides a means for actuating the articulating member of the tool by depressing the handle, which moves the actuating rod forward toward the distal end of the instrument. In the preferred embodiment, this actuating means serves to close the articulating member, such as one side of a pair of forceps.

The invention also provides an angular spring wire which functions as a means for biasing the lever in an open position. This feature allows the resistance and sensitivity of the lever to be varied by changing the thickness and resistance of the spring. The wire spring engages the handle at the point of attachment between the base and the lever arm, and engages the lever on its lower surface facing the base, biasing the lever in an open position. The wire is maintained in its aligned position relative to the base by being selectively recessed into a slot formed in the top surface of the base.

The invention further provides elongated ergonomically adapted finger pads on the sides of the base, which extend on either side below the bottom surface to terminate in support feet, which provide a stand for the surgical device. The base is further equipped with a rearward counterweight to counteract the weight of the tool on the opposite end.

Additionally, the pivot point (or hinged joint) of the handle of the invention is designed for easy manufacture, assembly and disassembly. The lever and base are cast from single molds which form complimentary portions of the joint. A single fixation screw forms a transverse pivot point which connects the actuator arm and base. The spring wire biasing means is simultaneously held in position in the joint without the need for additional screws or welds. The spring wire is retained in position between the actuator arm and a groove in the base when the fixation screw is in place such that the wire urges the lever into a normally open position.

Accordingly, it is an object of the invention to provide an improved handle for hand held surgical instruments of the type having a tool with at least one articulated member thereon wherein the handle has a means for actuating the articulated member.

It is a further object of the invention to provide an improved surgical instrument and instrument handle which is sensitive, responsive and ergonomically designed to augment the natrual motions of the human hand. In particular, it is an object of the invention to provide an instrument handle which fully utilizes the sensitive and delicate opposition capabilities of the thumb and index finger for movement of the lever arm of the instrument handle.

Another object of the invention is to provide an instrument handle which is designed for easy manufacture, assembly and disassembly, especially to allow for easy interchange of tensioning springs of varying strengths such that the sensitivity of the instrument handle can changed according to the needs of the surgeon.

A further object of the invention is to provide an instrument handle designed such that the means for connecting the lever arm and base forms the pivot point of the lever and simultaneously maintains the biasing means for the lever in proper position.

Another object of the invention is to provide an instrument handle with ergonomically adapted finger pads and support feet on the handle base which provide a stand for the instrument.

These and other features and objects of the present invention will become apparent in light of the specification as a whole.

DETAILED DESCRIPTION OF THE INVENTION

Figure 1:
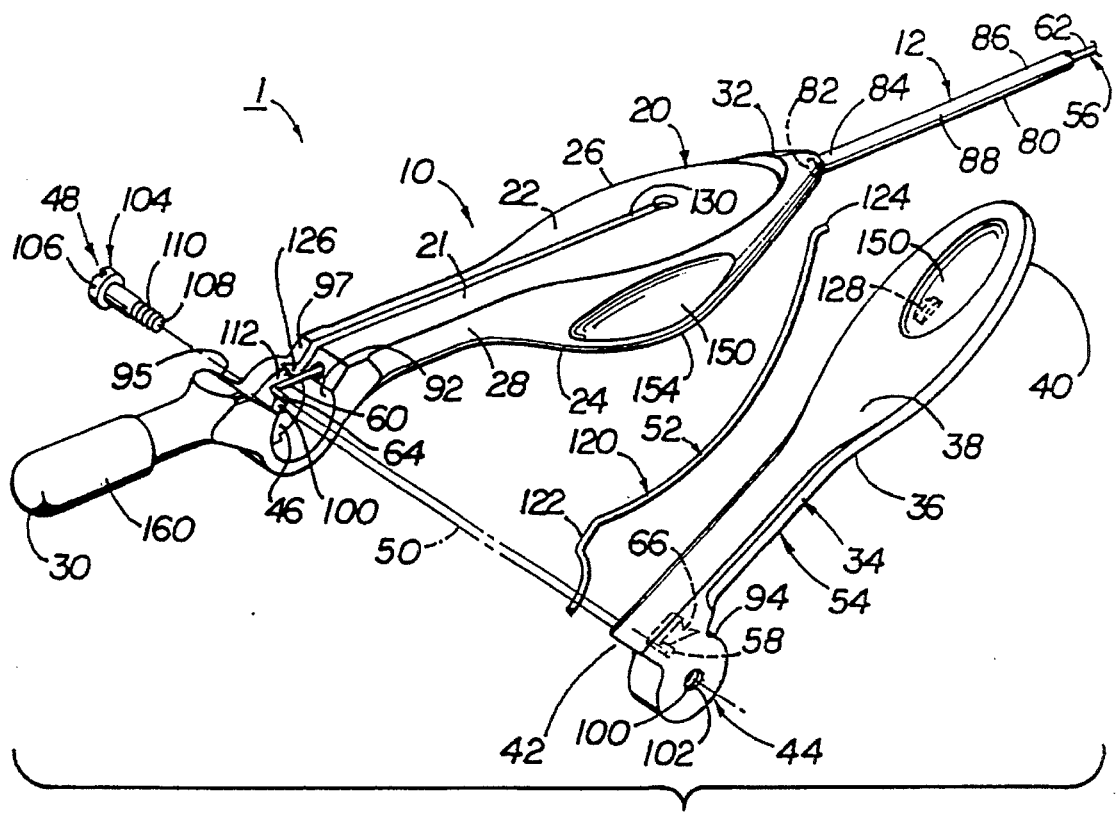
FIG. 1 is an exploded perspective view of the first embodiment of the present invention.
Figure 2:
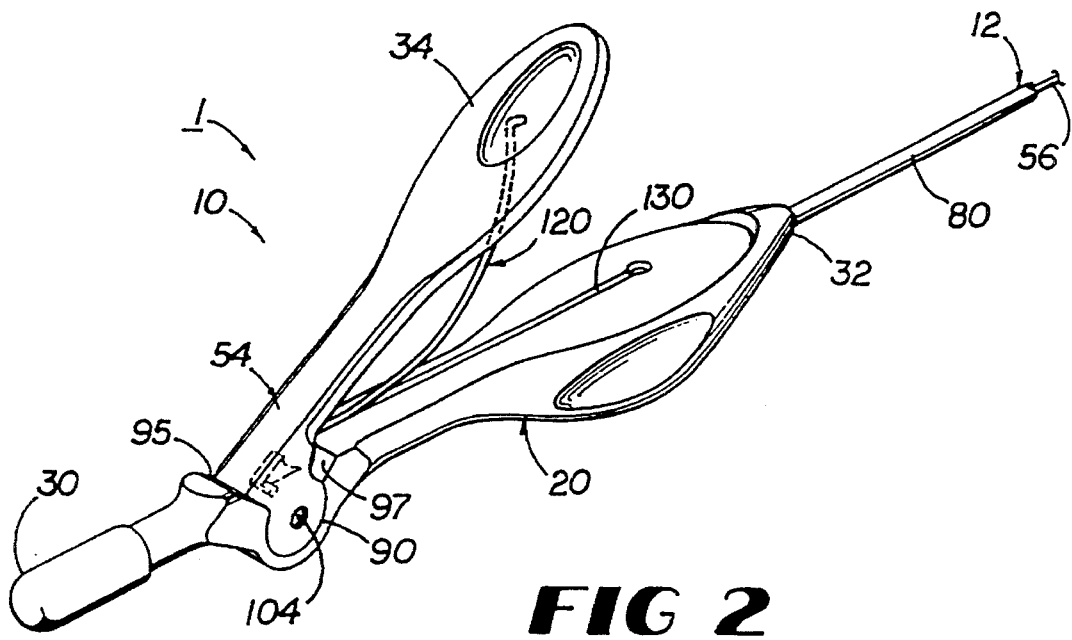
FIG. 2 is an assembled perspective view of the first embodiment showing the surgical instrument handle.
Figure 3:
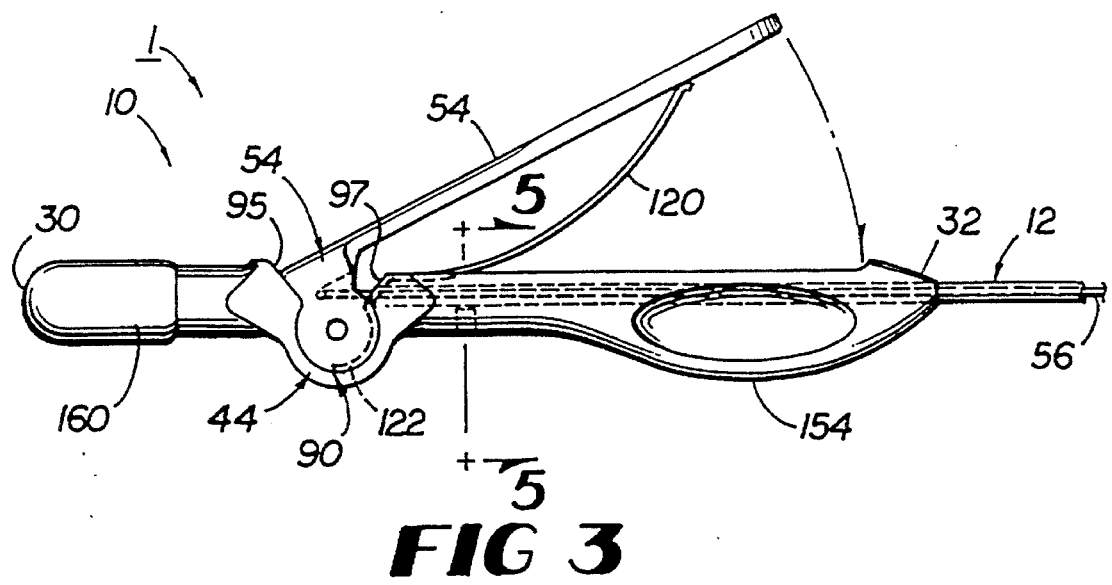
FIG. 3 is a side elevational view of the right side of the first embodiment of the surgical instrument handle in the open position.

The present invention may be understood more readily by reference to the following detailed description of specific embodiments and the Figures included herein. As used in the claims, "a", may mean one or more.

Referring now to FIGS. 1–4, the present invention provides a hand-held surgical instrument 1 comprising an improved handle 10 attached to a tool 12 having at least one articulated member (not shown) thereon. The tool 12 may be any one of a variety of a conventional surgical tools which has articulating, or moving, parts, such as scissors, hemostats, forceps, suture holders, biopsy retrievers, retractors, staplers and the like. The handle 10 has an elongated base 20 having a body portion 21, a top surface 22, opposite bottom surface 24, a first side 26 and an opposite second side 28, a proximal end 30 and a distal end 32. The handle 10 also has an elongated lever 34 having a first surface 36, an opposite second surface 38, a front end 40, a rear end 42 and an actuator arm 44 adjacent the rear end 42. The actuator arm 44 is adapted to be projected into the body portion 21 of said base 20 at a predetermined point 46. The predetermined point 46 may vary in position relative to the body portion 21 and the lever 34, depending upon the specific requirements of the surgeon and the tasks to be performed with the tool 12.

Figure 4:
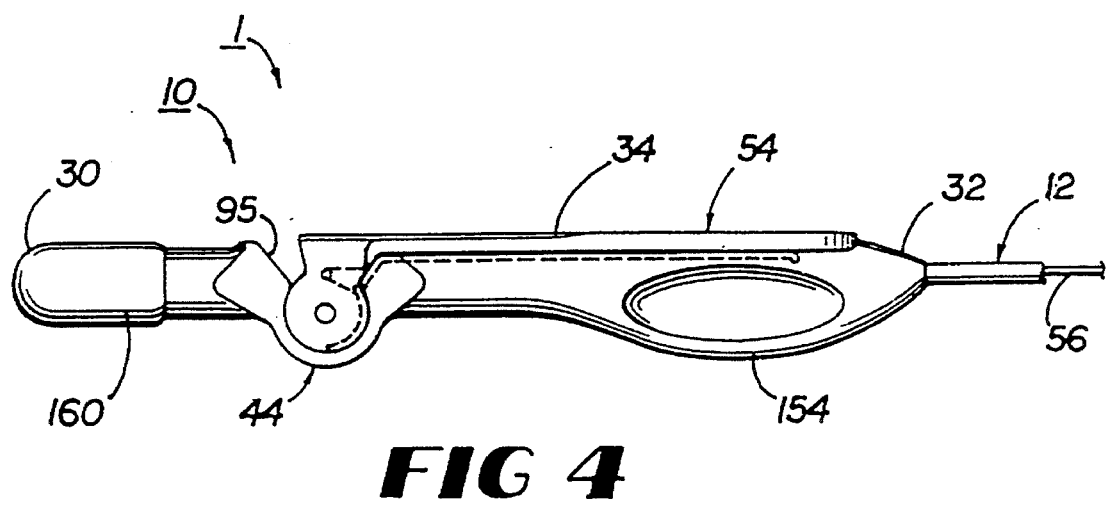
FIG. 4 is a side elevational view of the right side of the first embodiment of the surgical instrument handle with the lever in the closed position.

The handle 10 also has a means 48 for connecting said actuator arm 44 to said base 20 at the predetermined point 46 to allow said lever 34 to pivot about a linear transverse axis 50 at the predetermined point 46 between a normally open position (shown in FIG. 3) and a closed position (shown in FIG. 4). The base 20 and the lever 34 are juxtaposed to each other along their length, defining a longitudinal axis. The lever 34 extends forward along the longitudinal axis from said connecting means 48 toward the distal end 32 of said base 20, such that the first surface 36 of said lever 34 is adjacent to the top surface 22 of said body portion 21.

The handle 10 also has a means 52 for biasing said lever 34 in the normally open position. Additionally, the handle 10 is provided with a means 54 for actuating the articulated member (not shown) of the tool 12, wherein an actuator rod 56 is pivotally connected at a fixed point 58 on the actuator arm 44 of said lever 34 such that moving said lever 34 from the normally open position (FIG. 3) to the closed position (FIG. 4) causes said fixed point 58 on the actuator arm 44 to be displaced distally 32, thereby moving said actuator rod 56 toward the distal end 32 of the base 20, and causing movement of the articulated member (not shown). The fixed point 58 may be positioned in a variety of locations on the actuator arm 44 depending upon the range and force of actuating motion desired and the size and purpose of the tool 12.

In the first embodiment of the surgical instrument 1, shown in FIGS. 1–4, the actuator rod 56 further comprises a first end 60 and a second end 62, the second end 62 of said rod 56 being connected to the articulated member (not shown) of said tool 12 and the first end 60 of said rod 56 being connected to said actuator arm 44 at the fixed point 58. In this embodiment, the rod 56 is disposed through the body portion 21 of said base 20, such that movement of said lever 34 from the normally open position (FIG. 3) to the closed position (FIG. 4) causes the first end 60 of said rod 56 to be displaced toward the distal end 32 of said body portion 21 of said base 20, thereby moving the articulated member (not shown) of said tool 12.

In the first embodiment, the first end 60 of said actuator rod 56 comprises a pin 64 which is inserted into a complimentary receptacle 66 at the fixed point 58 on said actuator arm 44, thereby pivotally connecting said actuator arm 44 to said actuator rod 56. The pin 64 and complimentary receptacle 66 are shown to be round in shape, however, a variety of other shapes and configurations which permit a pivotal connection are contemplated.

Figure 6:
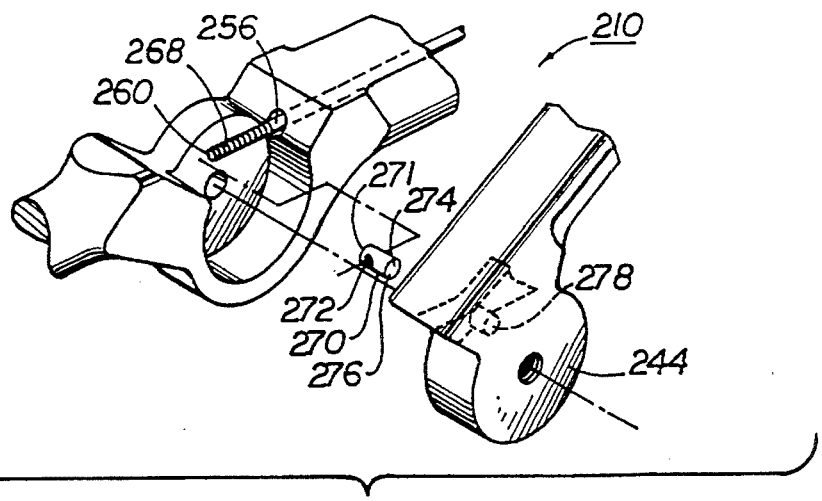
FIG. 6 is an exploded perspective view of a second embodiment of the invention showing an alternative actuating means comprising an actuator cuff.

Alternatively, referring to the second embodiment, shown in FIG. 6, the actuator rod 256 may be pivotally connected to the actuator arm 244 wherein the first end 260 of said actuator rod 256 comprises a threaded end 268, and further comprising a barrel-shaped actuator cuff 270 having a first end 271 with a complimentarily internally threaded opening 272 for receiving the threaded end 268 of the actuator rod 256, and having a second end 274 comprising a pin 276 which is inserted into a complimentary receptacle 178 at the fixed point 158 on the actuator arm 244. The pin 176 and actuator cuff 170 are shown to be round or barrel-shaped, however, a variety of other shapes and configurations which permit a pivotal connection are contemplated.

Figure 5:
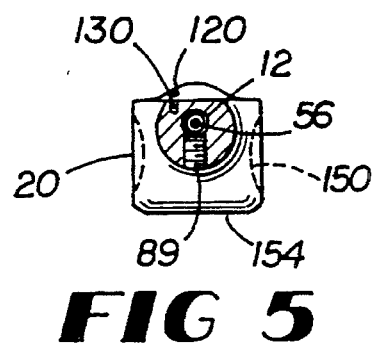
FIG. 5 is a sectional view of the present invention taken along lines 5—5 in FIG. 3.

Referring again to FIGS. 1–4, in the first embodiment, the tool 12 may further comprise a body member 80 wherein said base 20 defines an opening 82 at the distal end 32 thereof complementary to the shape of a first end 84 of the body member 80 of said tool 12, such that the body portion 21 of said base 10 attachably receives therein the first end 84 of said body member 80, and wherein said articulated member (not shown) is pivotally attached to an opposite second end 86 of said body member 80. Furthermore, in this preferred embodiment, said body member 80 of said tool 12 comprises a hollow elongated tube 88 having said actuator rod 56 slidably disposed therethrough. The slidable actuator rod 56 and tube 88 are of the type commonly used in the art for endoscopic instruments and the like, which require the movement of a tool which is attached to the second end 86 of tube 88. The invention also contemplates the absence of tube 88 such that the actuator rod 56 is slidably housed within a hollow elongated tube 88, but rather projects directly from the body 21 of the base 20 unhoused. In the sectional view of the first embodiment of the present invention shown in FIG. 5, a set screw 89 serves to secure the elongated tube 88 within the base 20. It is contemplated that the tube 88 can be journalled at the point of engagement of set screw 89 such that tube 88 and the associated tool can be rotated about the longitudinal axis of the handle.

The instrument 1 of the present invention further comprises a joint 90 for connecting the base 20 of the handle 10 to the actuator arm 44 of the lever 34 at the predetermined point 46. The joint 90 has a circular hinge socket 92 on said base 20 at the predetermined point 46 which is journalled for motion about the transverse axis 50, and a hinge barrel 94 on said actuator arm 44 dimensioned to be received within said hinge socket 92. By journalled, it is meant that the socket 92 has been configured, as by machine routing or original dye casting, to receive the hinge barrel 94. This joint 90 allows the actuator arm 44 to pivot about the transverse axis 50 at the predetermined point when said lever is moved between the normally open position (FIG. 3) and the closed position (FIG. 4). The configuration of the base 20 at the joint 90 also provides an open-lever stop 95 and a closed-lever stop 97, which define a maximum range of motion for the lever 34. The joint 90 is shown as a hinged socket, however, a variety of other joints are contemplated for pivotally connecting the base 20 to the lever 34 as would be apparent to one skilled in the art.

The connecting means 48 of the first embodiment comprises a continuous bore 100 extending along the transverse axis 50 through said base 20 at the predetermined point 46 and through said actuator arm 44. The bore 100 on said actuator arm 44 has internal threads 102 to receive a fixation screw 104 having a head end 106 and an opposite tail end 108 having threads 110 complimentary to said internal threads 102, said screw 104 passing through said bore 100 of said base 20 such that the head end 106 of said screw 104 rests within a countersink 112 on the first side 26 of said base 20. The connecting means 48 is shown as comprising a threaded fixation screw 104, however, a variety of other connecting means 48 are contemplated by the invention, such as bolts, rivets or other fasteners. The single connecting means 48 provides the invention with a greatly increased ease of assembly and disassembly.

The invention also provides a biasing means 52 for biasing the lever 34 in the normally open position, as shown in FIGS. 2, 3 and 7–9. The biasing means 52 of the first embodiment of the instrument 1 is a spring wire 120 having a pre-selected thickness and which is angularly positioned between the top surface 22 of said base 20 and the first surface 36 of said lever 34. The pre-selected thickness of the spring wire 120 is intended to vary according to the resistance and sensitivity desired by the surgeon for the particular tool 12. The spring wire 120 is maintained in elongated alignment with the handle 10 and lever 34 of the instrument 1 by being anchored to the base 20 by said connecting means 48 such that said spring wire 120 urges said lever 34 toward the normally open position. More specifically, the spring wire 120 has a first end 122 and a second end 124, and said base 20 has a recess 126 within said circular hinge socket 92 for receiving therein the first end 122 of said spring wire 120 such that the recess 126 and the connecting means 48 hold said spring wire 120 in elongated alignment with the longitudinal axis of handle 10 such that the second end 124 of said spring wire 120 is received within a slot 128 on the first surface 36 of said lever 34. Therefore, the spring wire 120 urges said lever 34 toward the normally open position. Additionally, the base 20 may further comprise an elongated recessed groove 130 on the top surface 22 thereof for receiving said spring wire 120 therein when said lever 34 is moved toward the closed position, such that said groove 130 guides and maintains said spring wire 120 in elongated alignment with said longitudinal axis. It should be appreciated that the connecting means 48 performs the simultaneous functions of connecting the base 20 and lever 34, securing the actuating means 54, and securing the biasing means 52.

Figure 7:
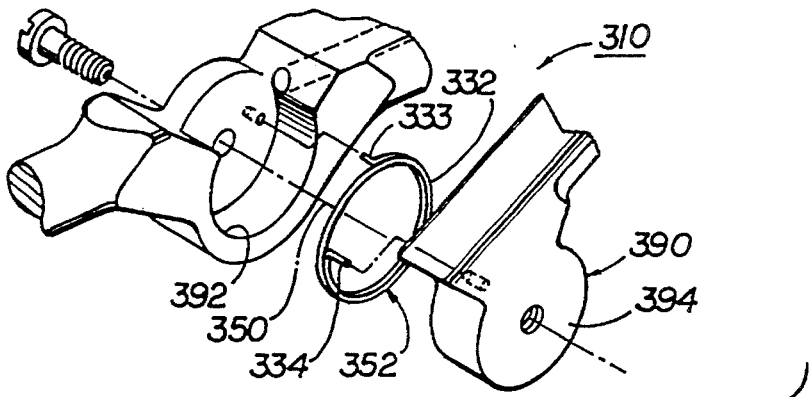
FIG. 7 is an exploded partial perspective view of a third embodiment of the invention showing an alternative biasing means comprising a torsion coil spring.

Furthermore, the invention contemplates a variety of alternative biasing means 52. In a third embodiment shown in FIG. 7, the biasing means 352 may be a torsion coil spring 332 positioned within the joint 390 between the circular hinge socket 392 and the hinge barrel 394 having a first end 333 attached to the base 320 within the circular hinge socket 392 and a second end 334 attached to the hinge barrel 394. As shown in FIG. 7, the tension coil spring 332 provides torque about the transverse axis 350 by providing force against the hinge barrel 394 in a counter-clockwise direction. This counter-clockwise force biases the handle 310 toward the normally open position.

Figure 8:
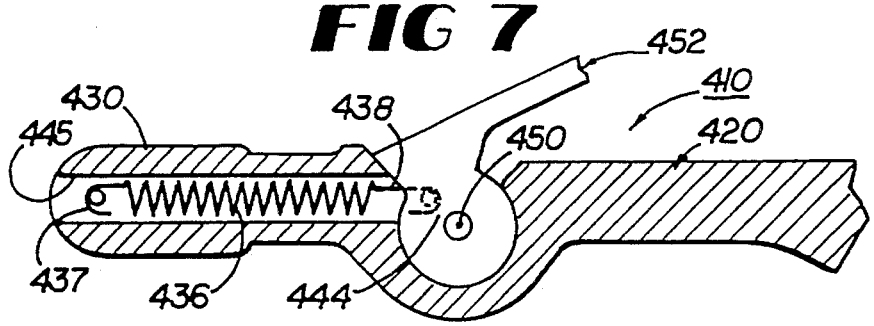
FIG. 8 is a longitudinal cross-section of a right side elevational view of a fourth embodiment of the invention showing an alternative biasing means comprising a tension spring.

In the fourth embodiment shown in FIG. 8, the biasing means 452 is a coil-type tension spring 436 having a proximal end 437 anchored adjacent to the proximal end 430 of the base 420 and having a distal end 438 anchored to the actuator arm 444 above the transverse axis 450. In the embodiment shown in FIG. 8, the tension spring 436 is anchored within a bore 445 of base 420. As shown in FIG. 8, the coil-type tension spring 436 provides torque about the transverse axis 450 by providing a pulling force on the hinge barrel 494 from above the transverse axis 450 in a counter-clockwise direction, and an opposing force pulling away from the proximal end 430 of the base 420. These opposing forces bias the handle 410 toward the normally open position. It is contemplated that the proximal end 436 of the tension spring 436 can be attached to a means for adjusting (increasing or decreasing) the tension of the spring 436. For example, a tension adjustment screw 537 of the type shown in FIG. 9 can be utilized to adjust the tension of spring 436.

Figure 9:
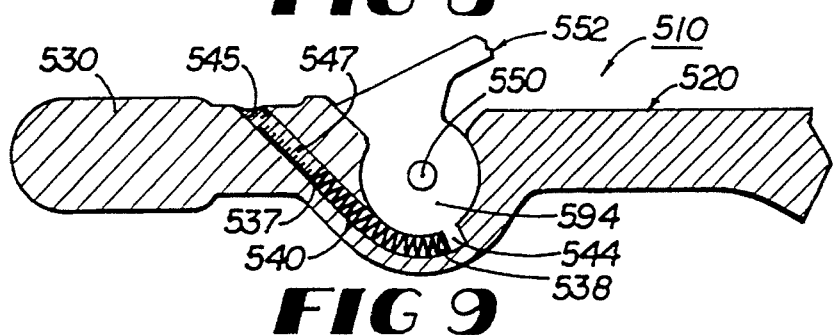
FIG. 9 is a longitudinal cross-section of a right side elevational view of a fifth embodiment of the invention showing an alternative biasing means comprising a compression spring.

In the fifth embodiment shown in FIG. 9, the biasing means 552 is a compression spring 540 having a proximal end 537 anchored adjacent to the proximal end 530 of the base 520 and having a distal end 538 anchored to the actuator arm 544 below the transverse axis 550. As shown in FIG. 9, the compression spring 540 provides torque about the transverse axis 550 by providing a pushing force on the hinge barrel 594 from below the transverse axis 550 in a counter-clockwise direction, and an opposing force pushing away from the proximal end 530 of the base 520. These opposing forces bias the handle 510 toward the normally open position. In the embodiment shown in FIG. 9, the proximal end 537 of the compression spring 540 is lo' anchored within a partially threaded bore 545, which allows increasing (or decreasing) of the spring tension by turning a complimentarily threaded tension adjustment screw 547 clockwise (or counter-clockwise).

The springs 120, 332, 436, 540 of the alternative embodiments may be of varying thicknesses or adapted for adjustable resistance depending on the sensitivity and tension desired by the surgeon for the particular tool. Furthermore, the anchoring points and configuration of the springs 120, 332, 436, 540 may vary as long as the handle 10, 310, 410, 510 is biased toward the normally open position.

As shown in FIG 1–FIG. 4, the first and second sides 26, 28 of the base 20 and the second surface 38 of the lever 34 each are equipped with an ergonomically adapted finger pad 150. These pads 150 assist the surgeon in maintaining a comfortable and secure grip on the instrument 1. In a preferred embodiment, the two sides 26, 28 of said base 20 each terminate in support feet 154 which allow the instrument 1 to stand independently. The base 20 can further comprise a counterweight 160 positioned within the proximal end 30 of the base 20 to balance said instrument 1 at a second predetermined point (not shown). The second predetermined point will vary depending upon the combination of the mass of the counterweight 160, the mass of the surgical tool 12 and the needs of the surgeon. It is contemplated that the second predetermined point could be adjusted in the surgeon's hand by rotating the counterweight 160, changing the distance between the counterweight 160 and the transverse axis 50 and thereby changing the balance point of the handle. For example, the counterweight 160 may be attached to the base 20 by means of an elongated threaded rod (not shown) on the base 20 which is received into a complimentarily threaded opening in the counterweight 1160. By rotating the counterweight 160 the distance between the counterweight 160 and the transverse axis 50 changes, and thus also the second predetermined point.

The invention also contemplates that the distal end 32 of the base 20 may be adapted for selective rotation about the longitudinal axis of the base 20, thereby allowing the surgical tool 12 to be selectively rotated.

It is contemplated by the present invention that the handle may be utilized on any suitable surgical instrument with an articulated member on the tool including, but not limited to, conventional hand-held surgical instruments and minimally invasive surgical instruments (endoscopic instruments). The instruments of the present invention may be constructed from any suitable material, such as metal or plastic. Examples of metals include stainless steel, aluminum and titanium. Examples of plastics include acetal, polycarbonate, ABS, and the like.

Although the present invention has been described with reference to specific details of certain embodiments thereof, it is not intended that such details should be regarded as limitations upon the scope of the invention except as and to the extent that they are included in the accompanying claims.

What is claimed is:

1. A hand-held surgical instrument comprising a handle attached to a tool having at least one articulated member thereon, the handle comprising:

a) an elongated base having a body portion, a top surface, opposite bottom surface, a first side and an opposite second side, a distal end a proximal end defining an inner portion;

b) an elongated lever having a first surface, an opposite second surface, a front end, a rear end and an actuator arm adjacent the rear end adapted to be projected into the inner portion of said base at a predetermined point;

c) means for connecting said actuator arm to said base at the predetermined point to allow said lever to pivot about a transverse axis at the predetermined point between a normally open position and a closed position, wherein said base and said lever are juxtaposed to each other along their length, with said lever extending forward from said connecting means toward the distal end of said base, such that the first surface of said lever is adjacent to the top surface of said body portion along a longitudinal axis thereof;

d) means connected to said lever for biasing said lever in the normally open position; and e) an actuator rod pivotally connected at a fixed point on the actuator arm of said lever such that moving said lever from the normally open position to the closed position causes said fixed point on the actuator arm to be displaced toward the distal end of said base, thereby moving said actuator rod distally and causing movement of the articulated member.

2. The instrument of claim 1, wherein said actuator rod further comprises a first end and a second end, the second end of said rod being connected to the articulated member of said tool and the first end of said rod being connected to said actuator arm at the fixed point, and wherein said rod is disposed through the body portion of said base such that movement of said lever from the normally open position to the closed position causes the first end of said rod to be displaced toward the distal end of said body portion of said base, thereby moving the articulated member of said tool.

3. The instrument of claim 2, wherein the first end of said actuator rod comprises a pin which is inserted into a complimentary receptacle at the fixed point on said actuator arm, thereby pivotally connecting said actuator arm to said actuator rod.

4. The instrument of claim 2, wherein the first end of said actuator rod comprises a threaded end and further comprising an actuator cuff comprising a first end comprising a complimentarily internally threaded opening for receiving the threaded end of the actuator rod, and a second end comprising a pin which is inserted into a complimentary receptacle at the fixed point on said actuator arm, thereby pivotally connecting said actuator arm to said actuator rod.

5. The instrument of claim 2, wherein the tool further comprises a body member and said base defines an opening at the distal end thereof complementary to the shape of a first end of the body member of said tool, such that the body portion of said base attachably receives therein the first end of said body member, and wherein said articulated member is pivotally attached to an opposite second end of said body member.

6. The instrument of claim 5, wherein a portion of said body member of said tool comprises a hollow elongated tube having said actuator rod slidably disposed therethrough.

7. The instrument of claim 1, further comprising a joint comprised of:

a) a circular hinge socket on said base at the predetermined point which is journalled for motion about the transverse axis; and b) a hinge barrel on said actuator arm dimensioned to be received within said hinge socket such that said actuator arm pivots about the transverse axis at the predetermined point when said lever is moved between the normally open position and the closed position.

8. The instrument of claim 7, wherein said connecting means comprises a continuous bore extending along the transverse axis through said base at the predetermined point and through said actuator arm, said bore on said actuator arm having internal threads to receive a fixation screw having a head end and an opposite tail end having threads complimentary to said internal threads, said screw passing through said bore of said base such that the head end of said screw rests within a countersink on the first side of said base.

9. The instrument of claim 1, wherein said biasing means comprises a spring wire having a pre-selected thickness angularly positioned between the top surface of said base and the first surface of said lever, and wherein said spring wire is maintained in elongated alignment with the instrument by being anchored to said base by said connecting means such that said spring wire urges said lever toward the normally open position.

10. The instrument of claim 7, wherein said biasing means comprises a spring wire having a first end and a second end and a preselected thickness, said wire being angularly positioned between the top surface of said base and the first surface of said lever, said base having a recess within said circular hinge socket for receiving therein the first end of said spring wire such that the recess and connecting means hold said spring wire in elongated alignment with said longitudinal axis such that the second end of said spring is received within a slot on the first surface of said lever, said spring wire urging said lever toward the normally open position.

11. The instrument of claim 10, wherein said base further comprises an elongated recessed groove on the top surface thereof for receiving said spring wire therein when said lever is moved toward the closed position such that said groove forms a guide for maintaining said spring wire in elongated alignment with said longitudinal axis.

12. The instrument of claim 7, wherein said biasing means comprises a torsion coil spring positioned within the joint between the circular hinge socket and the hinge barrel, said torsion coil spring comprising a first end attached to the circular hinge socket and a second end attached to the hinge barrel, such that the lever is biased in the normally open position.

13. The instrument of claim 7, wherein said biasing means comprises a tension spring within a hollow cavity in the base comprising a proximal end anchored internally adjacent to the proximal end of the base and having a distal end anchored to the actuator arm above the transverse axis, such that the lever is biased in the normally open position.

14. The instrument of claim 7, wherein said biasing means comprises a compression spring within a hollow cavity in the base comprising a proximal end anchored adjacent to the proximal end of the base and having a distal end anchored to the actuator arm below the transverse axis, such that the lever is biased in the normally open position.

15. The instrument of claim 1, wherein the first and second sides of the base and the second surface of the lever each further comprise an ergonomically adapted finger pad.

16. The instrument of claim 1, wherein the two sides of said base each terminate in support feet providing a stand for the instrument.

17. The instrument of claim 1, wherein said base further comprises a counterweight positioned adjacent the proximal end to balance said instrument at a second predetermined point.

18. The instrument of claim 1, wherein said instrument is an endoscopic surgical instrument.

* * * * *